US012582729B2

(12) United States Patent     (10) Patent No.: US 12,582,729 B2
Wadas et al.     (45) Date of Patent: Mar. 24, 2026

(54) KIT TECHNOLOGY FOR THE PRODUCTION AND LONG-TERM STORAGE OF Zr-89-PET RADIOPHARMACEUTICALS

(71) Applicant: Wake Forest University, Winston-Salem, NC (US)

(72) Inventors: Thaddeus J. Wadas, Winston-Salem, NC (US); Nikunj B. Bhatt, Winston-Salem, NC (US); Darpan N. Pandya, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 1160 days.

(21) Appl. No.: 16/964,377

(22) PCT Filed: Jan. 25, 2019

(86) PCT No.: PCT/US2019/015109
§ 371 (c)(1),
(2) Date: Jul. 23, 2020

(87) PCT Pub. No.: WO2019/147912
PCT Pub. Date: Aug. 1, 2019

(65) Prior Publication Data
US 2021/0046197 A1     Feb. 18, 2021

Related U.S. Application Data

(60) Provisional application No. 62/622,332, filed on Jan. 26, 2018.

(51) Int. Cl.
*A61K 51/10*     (2006.01)
*A61K 47/18*     (2017.01)
*A61K 51/04*     (2006.01)
*C07K 16/28*     (2006.01)
*C07K 16/32*     (2006.01)

(52) U.S. Cl.
CPC ........ *A61K 51/1093* (2013.01); *A61K 47/183* (2013.01); *A61K 51/0478* (2013.01); *C07K 16/2863* (2013.01); *C07K 16/32* (2013.01); *C07K 2317/24* (2013.01)

(58) Field of Classification Search
CPC ............... A61K 51/0478; A61K 45/06; A61K 51/1093; A61K 51/121; A61K 47/183; A61K 31/198; A61K 2300/00; C07K 16/2863; C07K 16/32; C07K 2317/24; A61P 35/00
See application file for complete search history.

(56) References Cited

U.S. PATENT DOCUMENTS

2010/0111856 A1*  5/2010  Gill ...................... C07C 323/60
                                                       424/1.49
2012/0065365 A1  3/2012  Chen et al.

FOREIGN PATENT DOCUMENTS

WO       2017/161356 A1     9/2017

OTHER PUBLICATIONS

Dijkers et al., J. Nucl. Med., 2009, 50(6), p. 974-981. (Year: 2009).*

* cited by examiner

*Primary Examiner* — Michael G. Hartley
*Assistant Examiner* — Leah H Schlientz
(74) *Attorney, Agent, or Firm* — FOX ROTHSCHILD LLP

(57)          ABSTRACT
The present invention is directed to radiopharmaceuticals with improved stability, a kit, and a method of production thereof.

14 Claims, 2 Drawing Sheets

KIT TECHNOLOGY FOR THE PRODUCTION AND LONG-TERM STORAGE OF Zr-89-PET RADIOPHARMACEUTICALS

RELATED APPLICATIONS AND CLAIM OF PRIORITY

The present application claims priority to and the benefit of U.S. Provisional Patent Application No. 62/622,332, filed Jan. 26, 2018. The entire contents of the priority application are incorporated herein by reference.

TECHNICAL FIELD

This application is directed to radiopharmaceuticals with improved stability, and specific activity and methods of preparation thereof.

BACKGROUND OF THE INVENTION

Currently, zirconium-89 ($^{89}$Zr: $t\frac{1}{2}$=78.4 h, $\beta^+$: 22.8%, $E_{\beta+max}$=901 keV; EC: 77%, $E_\gamma$=909 keV; 99%) is being utilized in more than 30 clinical trials involving precision medicine strategies designed to detect disease, stratify patients for appropriate treatment and monitor their response to therapy. For clinical applications, $^{89}$Zr is attached to a monoclonal antibody (mAb) exclusively through bifunctional chelator-derivatives of desferrioxamine (DFO). Early production methods were technically cumbersome involving sublimation or cation exchange. Recent approaches use phosphate buffered saline (PBS) as a reaction medium and a low DFO-mAb concentration. Still, many conventional methods have limitations since the mass of mAb, chelate-to-mAb ratio and reaction buffer vary between protocols. Moreover, there lacks literature reports on chromatographic analyses that adequately resolve high and low molecular weight impurities from the radiochemical product in the radiochromatogram. Finally, while $^{89}$Zr-DFO-mAb stability is influenced by environmental conditions such as time, temperature and storage medium, little guidance is available on preservation methods that protect radiopharmaceutical integrity during transport or long-term storage.

A need exists for improvised production methods for $^{89}$Zr-immuno-PET radiopharmaceuticals. It is also desirable that the radiopharmaceuticals can be stored over an extended time without sacrificing the purity and specific activity.

SUMMARY OF THE INVENTION

The present invention discloses a radiopharmaceutical, which exhibits multiple desirable properties such as significantly improved stability and specific activity in comparison with traditional agents of the same class. The comprehensively revised protocol for preparation of clinically relevant $^{89}$Zr-labeled antibodies find broad applications in medical industry, academic research and clinical studies. It is anticipated that the adoption of the production method described herein will improve the quality of care for patients needing PET-guided interventions, which are being rapidly integrated into precision medicine strategies.

An aspect of the invention provides a radiopharmaceutical system containing a complex and an effective amount of a radioprotectant to stabilize the complex. The complex comprises $^{89}$Zr coordinated to a chelator, wherein the chelator is conjugated to a monoclonal antibody, a mAb derivative (e.g. scFV, diabody, nanobody), a peptide, a protein, or a nanoparticle. The radioprotectant comprises N-acetyl-L-cysteine, L-methionine, or a combination thereof.

In some embodiments, the chelator is conjugated to an antibody, further wherein the ratio between the chelator and the antibody ranges from about 4:1 to about 2:1. In some embodiments, the $^{89}$Zr-labeled antibodies have a specific activity of at least about 0.144 MBq/µg. In some embodiments, the $^{89}$Zr-labeled antibodies have a purity (assessed by radio-size-exclusion chromatography) of at least about 97% for 7 days at 21° C. in the presence of the radioprotectant. In some embodiments, the $^{89}$Zr-labeled antibodies have a purity of at least about 95% for 3 days at 21° C. in the presence of the radioprotectant.

Another aspect of the invention provides a kit including
a) a chelator;
b) a monoclonal antibody, a mAb derivative, a peptide, or a nanoparticle, wherein the chelator and the monoclonal antibody, a peptide, or a nanoparticle are separate from each other in the kit or conjugated to each other in the kit;
c) $^{89}$Zr, wherein the $^{89}$Zr is coordinated to the chelator or is in the form of an independent salt; and
d) a radioprotectant comprising N-acetyl-L-cysteine, L-methionine, or a combination thereof.

Another aspect of the invention provides a method of preparing a complex, wherein the complex comprises $^{89}$Zr coordinated to a chelator, and the chelator is conjugated to a protein, comprising the steps of
a) reacting the chelator with the protein to form a conjugate;
b) mixing the $^{89}$Zr with the conjugate in a buffer (e.g. HEPES buffer) without pre-treating it with a base to form a reaction mixture;
c) incubating the reaction mixture to form $^{89}$Zr-labeled conjugate; and
d) purifying the $^{89}$Zr-labeled conjugate.

In some embodiments, the reaction mixture of step b) comprises a radioprotectant (stabilizer; e.g. L-methionine, or N-acetyl-L-cysteine). In some embodiments, step d) includes passing the $^{89}$Zr-labeled conjugate through a column. In some embodiments, the $^{89}$Zr-labeled conjugate is eluted down the column with an eluting solution containing a radioprotectant (stabilizer; e.g. L-methionine, or N-acetyl-L-cysteine). In some embodiments, the method further includes adding a radioprotectant (stabilizer; e.g. L-methionine, or N-acetyl-L-cysteine) to the purified complex or a solution thereof.

Another aspect of the invention discloses a method of treating or diagnosing a disease comprising administering to a subject an $^{89}$Zr-labeled conjugate or system described herein. Examples of diseases to be treated or diagnosed using this invention include but are not limited to cardiovascular disease; cancer; neurological diseases such as Parkinson's disease and Alzheimer's disease; infection; immune disorders; autoimmune diseases such as rheumatoid arthritis, psoriatic arthritis and lupus; fibrosing disorders; sarcoidosis and metabolic diseases such as diabetes and obesity.

DETAILED DESCRIPTION OF THE INVENTION

Figure 1A:
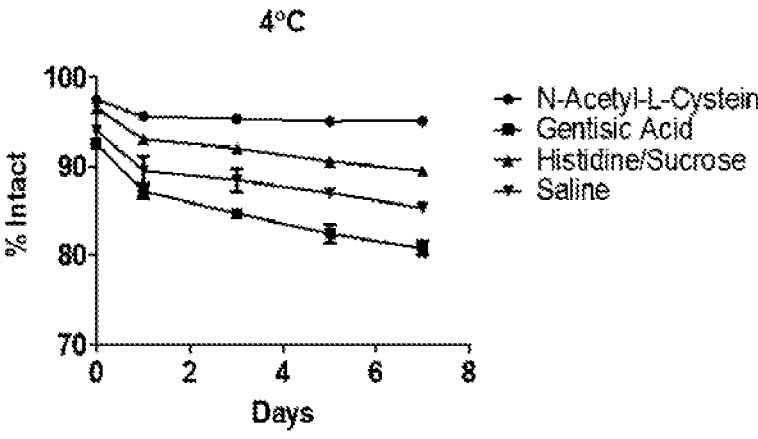
FIG. 1A illustrates the comparative stability of $^{89}$Zr-labeled antibody ($^{89}$Zr-DFO-cetuximab) at 4° C. in the presence of different buffer-excipient combinations. The radiopharmaceutical formulated in 0.25 M sodium acetate containing 0.5 mg·mL$^{-1}$ N-acetyl-L-cysteine underwent minimal degradation over the experimental time course, while the same radiopharmaceuticals formulated with 0.25 M sodium acetate containing 5 mg·mL$^{-1}$ gentisic acid, 20 mM histidine/240 mM sucrose or 0.9% saline were observed to be less stable over time. The percent intact radiopharmaceutical was determined by subtracting the total area under the product peak from the sum area generated for all peaks in the size exclusion chromatogram (SEC) and multiplying by a factor of 100%. Each data point is the average of three SEC runs.

This patent document describes a comprehensively revised protocol for the production, quality control and long-term storage of $^{89}$Zr-immuno-PET radiopharmaceuticals.

The production methods described herein offer several advantages over current protocols since they reduce the number of preparative steps and time necessary to synthesize $^{89}$Zr-immuno-PET agents, and this should reduce production costs. Additionally, these changes may facilitate the development of standardized kit technology that can be utilized at clinical sites where radiochemistry resources or technical expertise are unavailable and lead to greater access to clinical immuno-PET. N-acetyl-L-cysteine or L-methionine's superior protection of radiopharmaceutical integrity represents an additional improvement since enhanced stability should yield better image quality and provide clinicians with greater confidence in the data obtained from the clinical imaging enterprise. Further, the production protocol allows radiopharmaceuticals to be generated with significantly improved specific activity, which is an important outcome criterion in radiochemistry. Injection of a radiopharmaceutical that exhibits a high amount of radioactivity per unit mass reduces the possibility of a host response after agent injection, while ensuring favorable imaging contrast can be achieved during the clinical imaging session. Furthermore, radiopharmaceuticals with high and non-variable specific activity should face less scrutiny by regulatory agencies responsible for ensuring their safety and efficacy in the clinical setting.

While the following text may reference or exemplify specific embodiments of a compound or a method of treating a disease or condition, it is not intended to limit the scope of the compound or method to such reference or examples. Various modifications may be made by those skilled in the art, in view of practical and economic considerations, such as the substitutions of the compound and the amount or administration of the compound for treating or preventing a disease or condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "about" as used herein refers to the referenced numeric indication plus or minus 10% of that referenced numeric indication.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same. "Prophylactic treatment" is to be construed as any mode of treatment that is used to prevent progression of the disease or is used for precautionary purpose for persons at risk of developing the condition.

The term "subject" encompasses any animal, but preferably a mammal, e.g., human, non-human primate, a dog, a cat, a horse, a cow, or a rodent. More preferably, the subject is a human.

An aspect of the invention provides a system including an $^{89}$Zr-labeled conjugate and an effective amount of N-acetyl-L-cysteine, L-methionine, or a combination thereof to stabilize the $^{89}$Zr-labeled conjugate. The $^{89}$Zr-labeled conjugate contains $^{89}$Zr coordinated to a chelator, which is conjugated to a monoclonal antibody, a peptide, a protein, or a nanoparticle. The system can be a composition, a mixture, a solution, or a suspension. Various forms of engineered antibodies including, for example, diabodies, minibodies, single chain variable fragments, and nanobodies can be conjugated to the chelator. Non-liming examples of nanoparticles include particles comprising small molecule ligands, synthetic graft co-polymers, albumin, liposomes, quantum dots, carbon dots, nanorods, nanocages and similar structures composed of carbon, gold, silver, lanthanides, actinides or silicon. In some embodiments, the N-acetyl-cysteine is N-acetyl-L-cysteine (NAC). In some embodiments, the methionine is L-methionine (L-MET).

The system exhibits significantly improved specific activity and stability in comparison with many other compositions reported in the literature. In some embodiments, the specific activity is at least about 0.090, at least about 0.095, at least about 0.10, at least about 0.11, at least about 0.12, at least about 0.13, at least about 0.14, at least about 0.15, at least about 0.16, at least about 0.17, at least about 0.18, at least about 0.19, or at least about 0.20 MBq/μg.

The improved stability also distinguishes the present system from others in the field. In some embodiments, the system retains a purity for the $^{89}$Zr-labeled conjugate by more than about 80%, more than about 85%, more than about 90%, more than about 95%, or more than about 98% over time, which can be about 24 hours, about 48 hours, 3 days, 5 days or 7 days. The temperature for the time ranges from about 0° C. to about 10° C. or from about 15° C. to about 25° C. In some embodiments, the temperature over the time is about 5° C. or about 20° C.

The improved stability can be attributed to the presence of N-acetyl-cysteine or L-methionine as a radioprotectant agent. The exact amount of the radioprotectant agent depends on factors such as the amount of the $^{89}$Zr-labeled conjugate, the amount of radioactivity, the temperature and other components in the system. One of ordinary skill in the art can readily determine the amount of the radioprotectant agent without undue experiments. Analogs, derivatives, and isomers of the radioprotectant are also expressly contemplated as a protectant for the present system. In some embodiments, the radioprotectant (or stabilizer) consists essentially of L-methionine (L-MET) or N-acetyl-L-cysteine (NAC). In some embodiments, the stabilizer comprises L-methionine (L-MET) or N-acetyl-L-cysteine (NAC).

The system described herein can include a buffer solution. In some embodiments, the buffer is a sodium acetate solution.

Various chelators are suitable for the complex and are described herein. Examples include those described in PCT/US2017/023101, the entire disclosure of which is incorporated by reference herein. In some embodiments, the chelator is selected from the group consisting of desferrioxamine B (DFO), hydroxamates, catecholates, hydroxypyridinonates, terepthalamides, desferrichrome and their derivatives.

In some embodiments, the chelator is conjugated to a protein in the complex. In some embodiments, the chelator is conjugated to an antibody. In some embodiments, the antibody is an FDA approved antibody for cancer, arthritis, cardiovascular disease, metabolic diseases, autoimmune diseases, immunological diseases or neurodegenerative diseases. In some embodiments, the antibody is cetuximab or trastuzumab.

The ratio between the chelator and the protein or antibody generally ranges from about 6:1 to about 1:1. Exemplary ratios include about 5:1, about 4:1, about 3:1, and about 2:1, and about 3:2.

The ratio between the conjugate (of chelator and the protein or antibody) and $^{89}$Zr ranges from about 4:1 to about 1:1. In some embodiments, the ratio is about 3:1, about 2.5:1, about 2:1, or about 1.5:1.

Another aspect of the invention provides a kit, including
a) a chelator;
b) a protein, monoclonal antibody, a peptide, or a nanoparticle, wherein the chelator and the protein, monoclonal antibody, a peptide, or a nanoparticle are separate from each other (not conjugated to each other) in the kit or conjugated to each other in the kit;
c) $^{89}$Zr, wherein the $^{89}$Zr is coordinated to the chelator or in the form an independent salt without being coordinated to the chelator; and
d) radioprotectant comprising N-acetyl-L-cysteine, L-methionine or a combination thereof.

The scope and selection of the chelator, the protein, monoclonal antibody, a peptide, or a nanoparticle, and the radioprotectant (stabilizer) are as described above. The $^{89}$Zr is coordinated to the chelator or in an independent salt. In some embodiments, the chelator is conjugated to the protein, monoclonal antibody, a peptide, or a nanoparticle. In some embodiments, the chelator is not coordinated to the $^{89}$Zr in the kit until when an $^{89}$Zr-labeled conjugate needs to be prepared prior to the administration of the radiopharmaceutical.

The kit allows for quick and efficient preparation of the system described above. In some embodiments, the chelator and the protein or antibody are separately stored in the kit or unreacted with each other in the kit. In some embodiments, the chelator and the protein or monoclonal antibody are in a ratio ranging from about 8:1 to about 3:1. Exemplary ranges include about 7:1, about 6:1, about 5:1, about 4:1, and about 3:1. When needed, the two components can be reacted with each other to form a conjugate. The conjugate is then mixed with an $^{89}$Zr source (in the form of, for example, a salt such as Zr-oxalate) to form the $^{89}$Zr-labeled conjugate described above. The N-acetyl-L-cysteine can be added to the mixture before or after the complex is formed to improve its stability.

In some embodiments of the kit, the chelator and the protein or antibody are already conjugated in the kit. When needed, the conjugate is reacted with the $^{89}$Zr source to form an $^{89}$Zr-labeled conjugate. The stabilizer (e.g. L-methionine or N-acetyl-L-cysteine) is added to the mixture before or after the $^{89}$Zr-labeled conjugate is formed.

In some embodiments of the kit, $^{89}$Zr is chelated to the chelator, which is either separate from the protein or antibody or already in conjugation with the protein or antibody. N-acetyl-L-cysteine is added to the complex or before the formation of the complex. In some embodiments, the kit also includes a manual or guide for operation of the kit and its components.

In some embodiments, the $^{89}$Zr is in the form of an independent salt having a counter ion, which is chloride, oxalate, bromide, fluoride or acetyl acetonate (AcAc). In some embodiments, the kit also includes a buffer (e.g. HEPES) which obviates the need to neutralize the excess amount of acid with a base after formation of the $^{89}$Zr-labeled conjugate. The buffer can be added to a reaction mixture, pre-mixed with the stabilizer (N-acetyl-L-cysteine or L-Met), or stored in a separate compartment of the kit.

The kit can also contain additionally one or more therapeutic agents, diagnostic agents or other anti-neoplastic agents/compounds. The anti-neoplastic agents/compounds that can be used with the compounds of the present invention include cytotoxic compounds as well as non-cytotoxic compounds.

Another aspect of the invention discloses a method of preparing the complex or system described herein. The method includes the steps of
a) reacting the chelator with the protein to form a conjugate;
b) mixing the $^{89}$Zr source (e.g. a chloride or oxalate salt of $^{89}$Zr) with the conjugate in a suitable buffer (e.g. HEPES buffer) without pre-treating it with a base to form a reaction mixture;
c) incubating the reaction mixture to form an $^{89}$Zr-labeled conjugate; and
d) purifying the $^{89}$Zr-labeled conjugate.

The scope and selection of the chelator, protein, peptide, or antibody, and the source of $^{89}$Zr are the same as above. Besides HEPES as a buffer, other solutions can also be used as long as a reasonably constant reaction pH can be maintained. In some embodiments, large concentration of aqueous chloride anion is absent in the buffer solution. The use of the buffer obviates the need to remove excess acid by adding a base into the crude product. For example, the crude product can be directly loaded to a column (PD-10 column) or a filtration device to remove the excess acid (e.g. oxalic acid) without having to neutralize the acid with a base (e.g. sodium carbonate). In some embodiments, the reaction time is at least 50%, at least 60%, or at least 70% less than conventional methods using a base to remove the acid. Because of this optimization, the reaction yield and the radiochemical purity or specific activity (SA) are significantly improved. In some embodiments, the purifying step does not involve a base for neutralizing the acid.

The ratio between the chelator and the protein or antibody in the complex, the ratio between the conjugate and $^{89}$Zr, the stability, and the range of specific activity for the complex or system prepared with the above method are the same as described above. For example, the chelator and the protein prior to conjugation are in a ratio ranging from about 8:1 to about 3:1. Exemplary ranges include about 7:1, about 6:1, about 5:1, about 4:1, and about 3:1.

The reaction of step c) between the conjugate and $^{89}$Zr can be accomplished in a buffer containing a radioprotectant (e.g. N-acetyl-L-cysteine, L-Met or a combination thereof). The radioprotectant can also be added before or after the reaction.

The purification of the crude product can be accomplished by any method known in the art, including for example, filtration and elution from a column (e.g. PD-10 column). In some embodiments, the crude [89]Zr-labeled conjugate is eluted down the column with a buffer containing the radioprotectant (e.g. N-acetyl-L-cysteine). In some embodiments, the radioprotectant is added to the purified complex or a solution thereof.

Some of the basic steps relating to the preparation of starting materials and the formation of the complex can also reference international patent application PCT/US2017/023101, the entire disclosure of which is incorporated herein by reference.

Another aspect of this document discloses a method of treating or diagnosing a disease comprising administering to a subject a complex or system described herein. The disease to be treated or diagnosed includes cancer, cardiovascular, neurological, infectious, metabolic and autoimmune diseases. The exact formulation, route of administration and dosage for the complex or system can be chosen by the individual physician in view of the patient's condition. (see e.g., Fingl et al. 1975, in "The Pharmacological Basis of Therapeutics", which is hereby incorporated herein by reference in its entirety, with reference to Ch. 1, p. 1). Clinical workflow including, for example, tissue analysis for the determination of target expression, patient selection, dose design of mAb for optimal tumor targeting, pharmacokinetics measurement, dosimetry and patient compliance can be performed or evaluated without undue experiments.

EXAMPLES

Example 1

Reagent Setup

2 M Sodium carbonate: Dissolve 10.599 g of sodium carbonate in 35 mL of Milli-Q water and adjust volume to 50 mL with Milli-Q water.

20 mM Histidine/240 mM Sucrose: Dissolve 0.310 g of Histidine and 8.215 g of sucrose in 50 mL of Milli-Q water and adjust volume to 100 mL with Milli-Q water. Mix well and check the pH. Adjust to 5.5 to 5.8.

0.25 M Sodium acetate buffer containing 5 $mg \cdot mL^{-1}$ gentisic acid: Dissolve 3.4 g sodium acetate trihydrate and 0.5 g gentisic acid in 80 mL of Milli-Q water and adjust volume to 100 mL with Milli-Q water. Mix well and check the pH. Adjust to 5.5 to 5.7.

0.25 M Sodium acetate buffer containing 5 $mg \cdot mL^{-1}$ N-acetyl-L-cysteine: Dissolve 3.4 g sodium acetate trihydrate and 0.5 g N-acetyl-L-cysteine in 80 mL of Milli-Q water and adjust volume to 100 mL with Milli-Q water.

0.25 M Sodium acetate buffer containing 0.5 $mg \cdot mL^{-1}$ N-acetyl-L-cysteine: Dissolve 3.4 g sodium acetate trihydrate and 0.05 g N-acetyl-L-cysteine in 80 mL of Milli-Q water and adjust volume to 100 mL with Milli-Q water.

0.5 M HEPES buffer: Mix 20 mL of Milli-Q water with 20 mL of 1 M HEPES solution and check the pH. Adjust to 7.0 to 7.5.

50 mM EDTA (pH 5.0): Dissolve 1.46 g EDTA and 2.85 mL of 2 M $Na_2CO_3$ in 80 mL of Milli-Q water and adjust volume to 100 mL with Milli-Q water.

DFO-Bz-NCS solution: Dissolve 1.53 mg of DFO-Bz-NCS in 60 μL of DMSO.

$ZrCl_4$: Dissolve 7.87 mg of $ZrCl_4$ in 80 mL of Milli-Q water and adjust volume to 100 mL with Milli-Q water.

Protocols

A. Conjugation of DFO with mAbs

1. DFO-mAbs can be prepared using a reported procedure with modifications (Nat. Protoc. 2010; 5:739-43).
2. Aliquot 6 mg mAb in 1.5 mL eppendorf tube.
3. Add 600 μL saline to the tube.
4. Add 60 μL 0.1 M $Na_2CO_3$ (pH of mixture should be 8.9 to 9.1).
5. Add 6 μL of DFO-Bz-NCS solution (5-fold molar excess) to the antibody solution.
6. Incubate for 30 min. at 37° C. using a thermomixer set at 550 r.p.m.
7. Rinse a PD-10 column with 25 mL saline.
8. Load reaction mixture on PD-10 column and discard eluate.
9. Add 1.83 mL of eluent and discard eluate.
10. Add 2.2 mL of eluent and collect pure DFO-mAb in saline.
11. Store DFO-mAb at 4° C. for [89]Zr-radiolabeling.

B. Preparation of [89]Zr-DFO-mAbs without $Na_2CO_3$ Neutralization of the Reaction Solution and Using N-Acetyl-L-Cysteine as a Radioprotectant.

1. Add 1.3-1.5 mCi (48-55 MBq) of [[89]Zr]Zr-oxalate in 25-30 μL 1.0 M oxalic acid in 1.5 mL eppendorf tube.
2. Add 500 μL 0.5 M HEPES buffer (pH 7.2).
3. Add 100 μL 0.25 M sodium acetate buffer containing 5 $mg \cdot mL^{-1}$ N-acetyl-L-cysteine.
4. Add 330 μg (in 121 μL saline) of DFO-mAb conjugate.
5. Incubate for 15 min. at 21° C. using a thermomixer set at 550 r.p.m.
6. Rinse a PD-10 column with 25 mL of 0.25 M sodium acetate buffer containing 0.5 $mg \cdot mL^{-1}$ N-acetyl-L-cysteine.
7. Load reaction mixture on PD-10 column and discard eluate.
8. Add 1.83 mL of 0.25 M sodium acetate buffer containing 0.5 $mg \cdot mL^{-1}$ N-acetyl-L-cysteine and discard eluate.
9. Add 2.2 mL of 0.25 M sodium acetate buffer containing 0.5 $mg \cdot mL^{-1}$ N-acetyl-L-cysteine and collect pure [89]Zr-DFO-mAb in the eluate.

C. Determination of Chelator to Antibody Ratio

1. Chelator to antibody ratio was determined as previously described.
2. Add 10 μL of $ZrCl_4$ solution in 1.5 mL eppendorf tube.
3. Add ~50 μCi (0.19 MBq) of [[89]Zr]Zr-oxalate in 2-3 μL 1.0 M oxalic acid.
4. Add 1-2 μL of 2 M $Na_2CO_3$.
5. Incubate for 3 min. at 21° C. using a thermomixer set at 550 r.p.m.
6. Add 300 μL 0.5 M HEPES buffer (pH 7.2).
7. Add 50 μg (in 18.4 μL saline) of DFO-mAb conjugates.
8. Incubate for 20 min. at 21° C. using a thermomixer set at 550 r.p.m.
9. Add 50 μL 50 mM EDTA solution.
10. Incubate for 10 min. at 21° C. using a thermomixer set at 550 r.p.m.
11. Spot 2-3 μL of reaction mixture on ITLC-SG and develop with 50 mM EDTA (pH 5.0) as eluent.
12. Cut the ITLC strip at the middle to separate the origin and front.
13. Assess radioactivity at the origin and solvent front using a gamma counter.

14. Calculate chelator to antibody ratio using following equation.

$$\text{Moles of chelator} = \text{Moles of } ZrCl_4 \times \left( \frac{\text{cpm}(R_f < 0.5)}{\text{cpm(total)}} \right)$$

D. In Vitro Stability of $^{89}$Zr-DFO-mAb

1. Preserve 300 μL (0.25 mCi; 9 MBq) of $^{89}$Zr-DFO-mAb at 4° C. and 21° C.

2. At 1 d, 3 d, 5 d and 7 d intervals, inject samples (n=3) from each set in SE-HPLC with a 0.5 mL·min$^{-1}$ flow rate.

3. Collect HPLC-fractions (0.5 mL per tube).

4. Measure the activity in each tube using a gamma counter.

E. In Vitro Serum Stability of $^{89}$Zr-DFO-mAb.

1. Add 500 μL human serum in 1.5 mL eppendorf tube.

2. Add 50 μL (~50 μCi; 0.19 MBq) of $^{89}$Zr-DFO-mAb (in appropriate storage media) to the tube containing the human serum.

3. Incubate at 37° C. for 7 days.

4. At 1 d, 3 d, 5 d and 7 d intervals, take 4 μL of sample in 30 kDa centrifugal filter unit, add 96 μL of PBS solution (5% DMSO in PBS) and spin for 7 min.

5. Add 100 μL PBS solution in the filter unit and spin down for 7 min. Repeat this step once.

6. Count the activity in filter and filtrate by gamma counter.

7. Calculate % of intact $^{89}$Zr-DFO-mAb using the following equation.

$$\text{Intact } ^{89}Zr\text{-}DFO\text{-}mAb = 100 \times \left( \frac{\text{cpm (filter)}}{\text{cpm (total)}} \right)$$

Modified Preparative Route Used to Prepare $^{89}$Zr-DFO-mAbs.

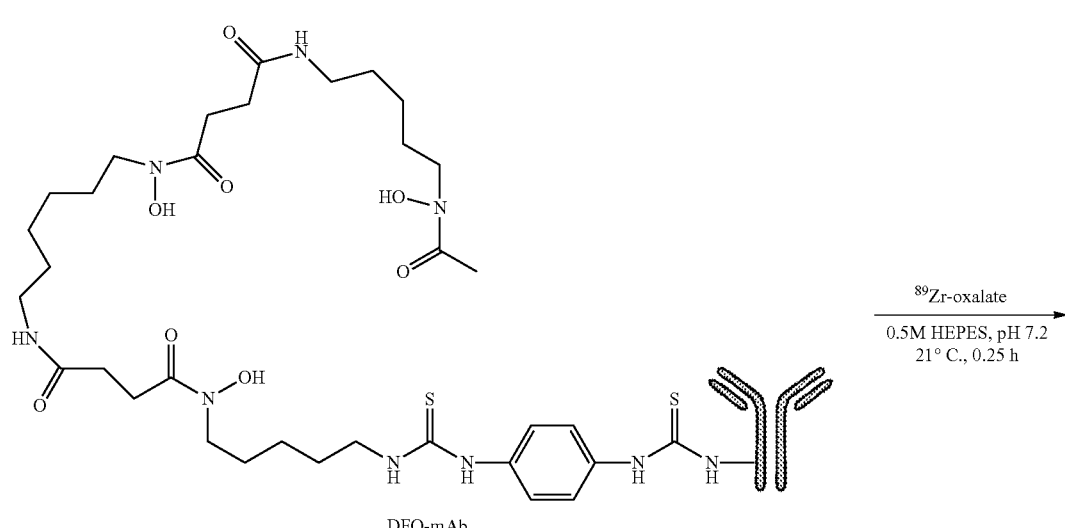

DFO-Bz-NCS

DFO-mAb

-continued $^{89}$Zr-DFO-mAb

In the examination of the conjugation efficiency of p-SCN-Bz-DFO to solvent accessible primary amine groups on the mAb surface, it was observed that a 5-molar excess of this reagent yielded an average of 3±1 chelators per antibody in as little as 30 minutes. A 5-molar excess seemed to offer a meaningful compromise since an excellent conjugation efficiency could be obtained while limiting the loss of the unreacted BFC reagent or exacerbating antibody aggregation that is often observed when larger concentrations of p-SCN-Bz-DFO are used during mAb conjugation. Table 1 compares the present optimized conditions with literature reports for generating radiopharmaceuticals. The amount of DFO-mAb conjugate used in the radiochemical synthesis was reduced to 2.5-fold. Cetuximab and trastuzumab were labelled quantitatively and with high specific activity. Additionally, it was observed that HEPES buffer was the most suitable reaction solvent for radiopharmaceutical preparation since large concentrations of aqueous chloride anion are absent. Interestingly, its buffering capacity was sufficient to maintain reaction pH, which allowed for oxalic acid removal from the radiochemistry reaction mixture by PD-10 column without the need for Na$_2$CO$_3$ addition beforehand. Eliminating this acid neutralization step reduced preparation time by 75% without compromising radiochemical yield, radiochemical purity or specific activity (SA) (Table 1) and represents a significant improvement over the current methodologies used to prepare these agents.

TABLE 1

Summarized comparison of conditions used to prepare $^{89}$Zr-immuno-PET agents

| Parameter | Reference[f,g] | Reference[b] | This work |
|---|---|---|---|
| mAb (mg)[a] | 0.7-3.0 | 0.1 | 0.33 |
| $^{89}$Zr added (MBq) | 37-185 | 10 | 50-55 |
| Oxalic acid neutralization method | 2M Na$_2$CO$_3$ | 1M Na$_2$CO$_3$ | None |
| Reaction buffer | 0.5M HEPES[b] | PBS[c] | 0.5M HEPES[b] |
| Final reaction pH | 6.8-7.2 | 7-8 | 6.8-7.2 |
| Reaction temperature (° C.) | 21-24 | 21-24 | 21-24 |
| Reaction time (h) | 1 | 1 | 0.25 |
| Radiolabeling yield (%) | >85 | 96.9 ± 3.3 | ≥97[d] |

TABLE 1-continued

Summarized comparison of conditions used to prepare $^{89}$Zr-immuno-PET agents

| Parameter | Reference[f,g] | Reference[b] | This work |
|---|---|---|---|
| Radiochemical purity (%) | >95 | >95 | ≥97[d] |
| Specific activity (A$_s$; MBq · µg$^{-1}$) | 0.067-0.086 | 0.1 ± 0.03 | 0.144 ± 0.003 (n = 10)[e] |

[a]Mass mAb used in radiochemical synthesis.
[b]pH 7.1-7.3
[c]pH 7.4.
[d]Unchelated $^{89}$Zr was not present in the original reaction mixture as determined by Radio-ITLC. Final purity and yield reflects the presence of high and low molecular weight species, which were additionally determined by SE-HPLC.
[e]$^{89}$Zr-DFO-trastuzumab (n = 5) and $^{89}$Zr-DFO-cetuximab (n = 5).
[f]Perk, L. R. et al. Eur. J. Nucl. Med. Mol. Imaging 37, 250-259 (2010).
[g]Vosjan, M. J. et al. Nat. Protoc. 5, 739-743 (2010).
[h]Knight, J. C. et al. Dalton Trans. 45, 6343-6347 (2016).

TABLE 2

Chelator to antibody ratio obtained using the isotopic dilution method

| Antibody | Chelator per antibody |
|---|---|
| Cetuximab | 3.48 ± 0.2 |
| Trastuzumab | 2.91 ± 0.1 |

Current measures using radioactive thin-layer chromatography (radio-TLC) only distinguish un-chelated $^{89}$Zr from all other radiolabeled species, and current size-exclusion chromatography (SEC) methods fail to adequately resolve high-molecular weight protein aggregates from the product in the SEC chromatogram. Since these species may constitute as much as 15% of the total reaction mixture and can impact the in vivo performance of the radiopharmaceutical, accurately quantifying them becomes a necessity. To improve quality control strategies used to quantify radiochemical purity, the present invention used a Superdex 200 Increase 10/300 GL column, and an isocratic mobile phase consisting of phosphate buffered saline (DPBS) to resolve the high and low molecular weight impurities from the radiochemical product giving us greater accuracy in determining their contributions to the overall reaction composition. Adoption of this method should improve existing analytical measures established for [89]Zr-immuno-PET agents within the clinical setting.

Figure 1B:
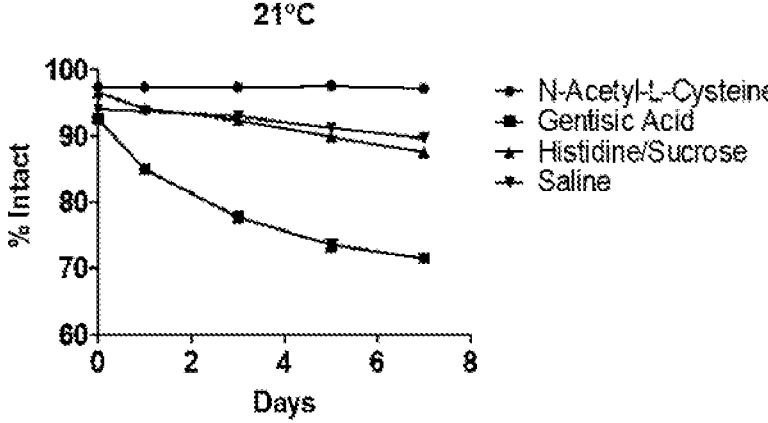
FIG. 1B illustrates the comparative stability of $^{89}$Zr-labeled antibody ($^{89}$Zr-DFO-cetuximab) at 21° C.
Figure 1C:
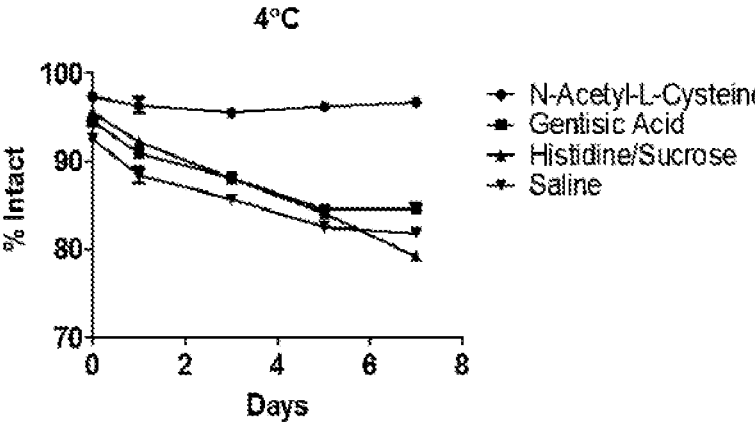
FIG. 1C illustrates the comparative stability of $^{89}$Zr-labeled antibody ($^{89}$Zr-DFO-trastuzumab) at 4° C.
Figure 1D:
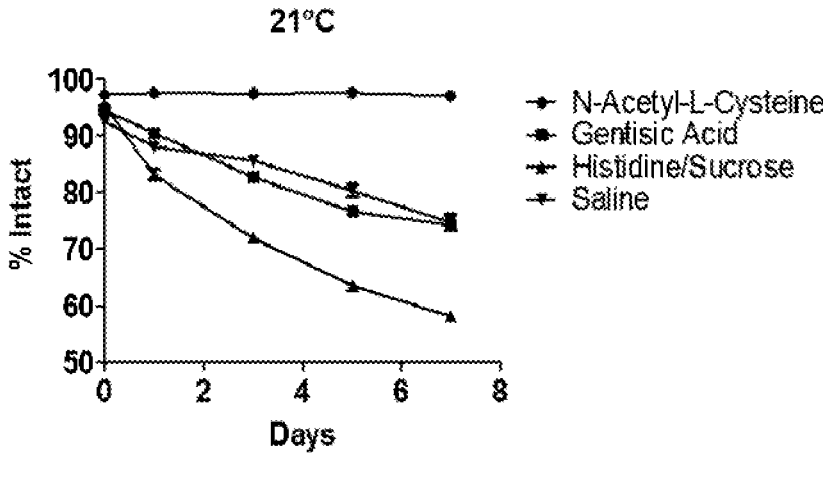
FIG. 1D illustrates the comparative stability of $^{89}$Zr-labeled antibody ($^{89}$Zr-DFO-trastuzumab) at 21° C.

The present invention also improved the long-term stability of [89]Zr-immuno-PET agents. Literature protocols have described their storage in 0.9% saline, 20 mM histidine/240 mM sucrose or 0.25 M sodium acetate buffer supplemented with 5 mg·mL$^{-1}$ 2,5-dihydroxybenzoic acid (gentisic acid; GA). Although formulation in 0.9% saline is nearly ideal for clinical injection, storage in this media is not advised since the radiolysis of water in the presence of a large chloride anion (Cl$^-$) concentration generates hydroxyl radical (·OH) and hypochlorous acid (HOCl), which are believed to be detrimental to radiopharmaceutical integrity. A 20 mM histidine/240 mM sucrose solution has also been suggested, but this buffer-excipient combination is not perceived to be an effective radioprotectant and the exact mechanism by which it protects the antibody in solution remains unknown. Finally, even though 0.25 M sodium acetate containing 5 mg·mL$^{-1}$ GA is more effective at protecting the radiolabeled antibody in solution compared to the prior two, it is still sub-optimal since the calculated rate constant describing the reaction between GA and the ·OH is smaller than the rate constant describing the latter's reaction with thiourea, which is a common functional group linking DFO to the mAb. Including a more powerful antioxidant in the radiopharmaceutical formulation would be beneficial. Accordingly, the stability of [89]Zr-DFO-cetuximab and [89]Zr-DFO-trastuzumab over seven days were compared while being stored in 0.9% saline, 20 mM histidine/240 mM sucrose, 0.25 M sodium acetate containing 5 mg·mL$^{-1}$ GA or 0.25 M sodium acetate containing NAC. The results of these studies are presented in FIG. 1 and Tables 3-6. After 24 h at either 4° C. or 21° C., both radiolabeled antibodies formulated with 0.25 M sodium acetate containing 5 mg·mL$^{-1}$ NAC exhibited radiochemical purities that were greater than 95%. Moreover, they did not undergo significant degradation during the seven-day study. Conversely, SEC revealed increasing amounts of high- and low-molecular weight impurities in samples of [89]Zr-labeled mAbs formulated with the other three buffer-excipient combinations over the same study period and suggests that NAC may provide superior protection from radical induced damage during the transport and storage of [89]Zr-immuno-PET agents. Stability shown in FIG. 1 was determined using the size exclusion chromatography method. [39]Zr-DFO-cetuximab (A, B) or [89]Zr-DFO-trastuzumab (C, D) formulated in 0.25 M sodium acetate containing 0.5 mg·mL$^{-1}$ N-acetyl-L-cysteine underwent minimal degradation over the experimental time course, while the same radiopharmaceuticals formulated with 0.25 M sodium acetate containing 5 mg·mL$^{-1}$ gentisic acid, 20 mM histidine/240 mM sucrose or 0.9% saline were observed to be less stable over time. The percent intact radiopharmaceutical was determined by subtracting the total area under the product peak from the sum area generated for all peaks in the size exclusion chromatogram and multiplying by a factor of 100%. Each data point is the average of three SEC runs.

TABLE 3

Summary of optimized mAb mass used to prepare [89]Zr-DFO-mAbs[a]

| Conjugates (DFO-mAbs) | Mass of conjugate (μg) | [89]Zr(ox)$_2$ added (MBq) | Radiochemical purity[b] by Radio-ITLC (%) | Radiochemical yield[c] (%) | Radiochemical purity[c] by SE-HPLC (%) | Specific activity (A$_s$; MBq μg$^{-1}$) |
|---|---|---|---|---|---|---|
| DFO-cetuximab | 500 | 55.3 | 99.9 ± 0.1 | 98.8 ± 0.2 | 98.7 ± 0.3 | 0.109 ± 0.001 |
| | 400 | 55.1 | 99.8 ± 0.2 | 98.2 ± 0.3 | 98.3 ± 0.3 | 0.134 ± 0.002 |
| | 350 | 50.2 | 99.9 ± 0.1 | 97.8 ± 0.4 | 97.9 ± 0.5 | 0.139 ± 0.004 |
| | 330 | 49.8 | 99.9 ± 0.2 | 97.3 ± 0.4 | 97.5 ± 0.4 | 0.144 ± 0.003 |
| | 300 | 48.1 | 99.8 ± 0.3 | 95.2 ± 0.5 | 95.5 ± 0.7 | 0.151 ± 0.002 |
| DFO-trastuzumab | 500 | 55.2 | 99.8 ± 0.1 | 98.5 ± 0.3 | 98.6 ± 0.2 | 0.108 ± 0.001 |
| | 400 | 54.6 | 99.9 ± 0.2 | 98.0 ± 0.2 | 98.1 ± 0.5 | 0.131 ± 0.004 |
| | 350 | 50.4 | 99.7 ± 0.4 | 97.6 ± 0.6 | 97.8 ± 0.4 | 0.139 ± 0.002 |
| | 330 | 49.9 | 99.9 ± 0.1 | 97.5 ± 0.5 | 97.7 ± 0.5 | 0.145 ± 0.002 |
| | 300 | 47.9 | 99.8 ± 0.2 | 94.9 ± 0.4 | 95.1 ± 0.6 | 0.150 ± 0.002 |

[a]DFO-mAbs were labeled with [[89]Zr]Zr-oxalate using 0.5M HEPES buffer (500 μL, pH 7.2) and N-acetyl-L-cysteine (100 uL, 5 mg · mL$^{-1}$ in 0.5M sodium acetate, pH 6.8-7.0) at 21° C. for 15 min.
[b]Unchelated [89]Zr was not present in the original reaction mixture as determined by Radio-ITLC.
[c]Final purity and yield reflect the presence of high and low molecular weight species, which were additionally determined by SE-HPLC.

TABLE 4

Summary of SEC data describing the chronological stability of [89]Zr-DFO-cetuximab formulated in different buffer-excipient combinations (n = 3 for each buffer-excipient combination at each time point)

| | | Species % | | | | | | |
|---|---|---|---|---|---|---|---|---|
| | | 0.9% Saline | | | 20 mM Histidine/240 mM Sucrose | | | 0.25M NaOAc + |
| Time point | Temp. (° C.) | HMW[c] | Intact radiotracter | LMW[d] | HMW[c] | Intact radiotracter | LMW[d] | 5 mg · mL$^{-1}$ GA[a] HMW[c] |
| 0 h | 21 | 6.0 | 94.0 | 0.0 | 3.5 | 96.5 | 0.0 | 7.5 |
| 1 d | 4 | 9.9 ± 1.7 | 89.5 ± 1.6 | 0.7 ± 0.1 | 6.5 ± 0.1 | 93.0 ± 0.1 | 0.7 ± 0.1 | 9.5 ± 0.8 |
| | 21 | 5.3 ± 0.3 | 93.7 ± 0.2 | 1.1 ± 0.1 | 4.8 ± 0.1 | 94.1 ± 0.2 | 1.2 ± 0.1 | 9.2 ± 0.4 |
| 3 d | 4 | 10.9 ± 1.2 | 88.4 ± 1.3 | 0.8 ± 0.1 | 6.7 ± 0.1 | 92.0 ± 0.1 | 1.5 ± 0.1 | 10.1 ± 0.1 |
| | 21 | 5.8 ± 0.1 | 92.9 ± 0.1 | 1.3 ± 0.1 | 5.3 ± 0.1 | 92.3 ± 0.3 | 2.4 ± 0.1 | 11.6 ± 0.5 |

TABLE 4-continued

Summary of SEC data describing the chronological stability of $^{89}$Zr-DFO-cetuximab formulated in different buffer-excipient combinations (n = 3 for each buffer-excipient combination at each time point)

| | | | | | | | | |
|---|---|---|---|---|---|---|---|---|
| 5 d | 4 | 12.0 ± 0.1 | 87.0 ± 0.2 | 1.1 ± 0.1 | 7.4 ± 0.1 | 90.5 ± 0.1 | 2.3 ± 0.2 | 11.8 ± 0.6 |
| | 21 | 6.8 ± 0.3 | 91.2 ± 0.2 | 2.1 ± 0.1 | 5.9 ± 0.1 | 89.8 ± 0.5 | 4.4 ± 0.4 | 13.1 ± 0.1 |
| 7 d | 4 | 13.4 ± 0.4 | 85.3 ± 0.4 | 1.4 ± 0.1 | 7.6 ± 0.1 | 89.5 ± 0.1 | 3.1 ± 0.1 | 13.3 ± 0.4 |
| | 21 | 7.2 ± 0.3 | 89.6 ± 0.2 | 3.3 ± 0.1 | 6.2 ± 0.2 | 87.5 ± 0.6 | 6.4 ± 0.4 | 12.9 ± 0.1 |

| | | Species % | | | | | |
|---|---|---|---|---|---|---|---|
| | | 0.25M NaOAc + 5 mg · mL$^{-1}$ GA[a] | | | 0.25M NaOAc + 0.5 mg · mL$^{-1}$ NAC[b] | | |
| Time point | Temp. (° C.) | Intact radiotracter | LMW[d] | HMW[c] | Intact radiotracter | LMW[d] | |
| 0 h | 21 | 92.5 | 0.0 | 2.6 | 97.4 | 0.0 | |
| 1 d | 4 | 87.2 ± 0.8 | 3.4 ± 0.1 | 4.2 ± 0.2 | 95.6 ± 0.1 | 0.3 ± 0.1 | |
| | 21 | 84.9 ± 0.3 | 6.0 ± 0.7 | 2.1 ± 0.4 | 97.3 ± 0.2 | 0.6 ± 0.0 | |
| 3 d | 4 | 84.7 ± 0.1 | 5.3 ± 0.2 | 4.3 ± 0.3 | 95.3 ± 0.3 | 0.3 ± 0.0 | |
| | 21 | 77.7 ± 0.6 | 10.8 ± 1.1 | 2.1 ± 0.1 | 97.3 ± 0.0 | 0.6 ± 0.1 | |
| 5 d | 4 | 82.4 ± 1.0 | 5.9 ± 1.6 | 4.7 ± 0.4 | 95.0 ± 0.4 | 0.4 ± 0.0 | |
| | 21 | 73.5 ± 0.8 | 13.5 ± 0.8 | 1.9 ± 0.1 | 97.5 ± 01 | 0.6 ± 0.0 | |
| 7 d | 4 | 80.8 ± 0.8 | 6.0 ± 0.5 | 4.6 ± 0.1 | 95.1 ± 0.1 | 0.4 ± 0.0 | |
| | 21 | 71.5 ± 0.3 | 15.7 ± 0.1 | 2.1 ± 0.1 | 97.2 ± 0.1 | 0.8 ± 0.1 | |

[a]Gentisic acid.
[b]N-acetyl-L-cysteine.
[c]High-molecular weight, radioactive protein species.
[d]Low-molecular weight, radioactive protein species, or unchelated $^{89}$Zr.

TABLE 5

Summary of SEC data describing the chronological stability of $^{89}$Zr-DFO-trastuzumab formulated in different buffer-excipient combinations (n = 3 for each buffer-excipient combination at each time point)

| | | Species % | | | | | | |
|---|---|---|---|---|---|---|---|---|
| | | 0.9% Saline | | | 20 mM Histidine/240 mM Sucrose | | | 0.25M NaOAc + |
| Time point | Temp. (° C.) | HMW[c] | Intact radiotracter | LMW[d] | HMW[c] | Intact radiotracter | LMW[d] | 5 mg · mL$^{-1}$ GA[a] HMW[c] |
| 0 h | 21 | 7.7 | 92.3 | 0.0 | 4.6 | 95.4 | 0.0 | 5.6 |
| 1 d | 4 | 10.5 ± 1.3 | 87.7 ± 1.0 | 1.8 ± 0.4 | 6.1 ± 0.7 | 91.2 ± 0.6 | 2.7 ± 0.1 | 7.5 ± 0.4 |
| | 21 | 5.9 ± 0.1 | 87.4 ± 0.1 | 6.6 ± 0.1 | 2.7 ± 0.2 | 82.7 ± 0.7 | 14.7 ± 1.1 | 6.1 ± 0.2 |
| 3 d | 4 | 12.5 ± 0.3 | 84.9 ± 0.1 | 2.6 ± 0.3 | 5.9 ± 0.4 | 86.6 ± 0.6 | 7.4 ± 1.1 | 9.5 ± 0.3 |
| | 21 | 5.6 ± 0.1 | 84.9 ± 0.1 | 9.5 ± 0.1 | 2.3 ± 0.1 | 71.3 ± 0.2 | 26.5 ± 0.4 | 10.3 ± 0.7 |
| 5 d | 4 | 14.6 ± 0.2 | 81.4 ± 0.2 | 4.4 ± 0.1 | 6.1 ± 0.5 | 81.6 ± 0.6 | 12.4 ± 0.2 | 12.9 ± 0.1 |
| | 21 | 5.6 ± 0.1 | 79.5 ± 1.1 | 14.9 ± 1.1 | 2.6 ± 0.3 | 62.6 ± 0.2 | 34.9 ± 0.1 | 13.3 ± 0.1 |
| 7 d | 4 | 13.1 ± 0.2 | 80.3 ± 0.9 | 6.6 ± 1.0 | 6.4 ± 0.3 | 78.4 ± 0.2 | 15.3 ± 0.1 | 12.4 ± 0.1 |
| | 21 | 6.7 ± 0.1 | 73.8 ± 1.2 | 19.5 ± 1.4 | 3.2 ± 0.2 | 57.1 ± 0.2 | 39.8 ± 0.1 | 13.2 ± 0.7 |

| | | Species % | | | | | |
|---|---|---|---|---|---|---|---|
| | | 0.25M NaOAc + 5 mg · mL$^{-1}$ GA[a] | | | 0.25M NaOAc + 0.5 mg · mL$^{-1}$ NAC[b] | | |
| Time point | Temp. (° C.) | Intact radiotracter | LMW[d] | HMW[c] | Intact radiotracter | LMW[d] | |
| 0 h | 21 | 94.4 | 0.0 | 2.7 | 97.3 | 0.0 | |
| 1 d | 4 | 90.2 ± 0.3 | 2.1 ± 0.1 | 3.5 ± 0.0 | 96.3 ± 0.9 | 0.3 ± 0.0 | |
| | 21 | 89.9 ± 0.1 | 5.1 ± 0.4 | 2.0 ± 0.4 | 97.6 ± 0.2 | 0.5 ± 0.0 | |
| 3 d | 4 | 87.5 ± 0.2 | 2.9 ± 0.1 | 3.3 ± 0.1 | 96.5 ± 0.1 | 0.3 ± 0.0 | |
| | 21 | 82.2 ± 0.2 | 7.6 ± 0.6 | 2.0 ± 0.1 | 97.5 ± 0.0 | 0.5 ± 0.1 | |
| 5 d | 4 | 83.8 ± 0.1 | 3.2 ± 0.1 | 3.4 ± 0.4 | 96.2 ± 0.4 | 0.3 ± 0.0 | |
| | 21 | 76.2 ± 0.1 | 10.5 ± 0.2 | 1.7 ± 0.1 | 97.6 ± 0.1 | 0.7 ± 0.1 | |
| 7 d | 4 | 84.1 ± 0.6 | 3.6 ± 0.6 | 2.9 ± 0.1 | 96.7 ± 0.1 | 0.4 ± 0.1 | |
| | 21 | 73.9 ± 0.6 | 12.9 ± 1.2 | 2.1 ± 0.1 | 97.1 ± 0.2 | 0.9 ± 0.1 | |

[a]Gentisic acid.
[b]N-acetyl-L-cysteine.
[c]High-molecular weight, radioactive protein species.
[d]Low-molecular weight, radioactive protein species, or unchelated $^{89}$Zr.

TABLE 6

Chronological in vitro serum stability study data
of $^{89}$Zr-DFO-mAbs maintained at 37° C. (n =
3 for each radiopharmaceutical at each time point)

| Time point | [$^{89}$Zr]Zr-DFO-cetuximab | | [$^{89}$Zr]Zr-DFO-trastuzumab | |
|---|---|---|---|---|
| | % Intact | % Unchelated $^{89}$Zr | % Intact | % Unchelated $^{89}$Zr |
| 0 h | 99.9 | 0.1 | 99.9 | 0.1 |
| 1 d | 99.5 ± 0.1 | 0.4 ± 0.1 | 99.5 ± 0.1 | 0.5 ± 0.1 |
| 3 d | 99.2 ± 0.2 | 0.9 ± 0.1 | 99.4 ± 0.1 | 0.6 ± 0.2 |
| 5 d | 99.1 ± 0.5 | 1.0 ± 0.6 | 99.3 ± 0.2 | 0.7 ± 0.1 |
| 7 d | 98.9 ± 0.5 | 1.1 ± 0.3 | 99.3 ± 0.3 | 0.7 ± 0.1 |

Example 2

Zirconium-89 chloride ($^{89}$ZrCl$_4$) was prepared. Typically, 1,850 MBq of $^{89}$Zr(ox)$_2$ was loaded on the ion exchange cartridge, eluted as $^{89}$ZrCl$_4$ in 500 µL of 1 M HCl with a 99% recovery yield. The conversion process took 10 minutes to complete and the resulting $^{89}$ZrCl$_4$ was used to prepare $^{89}$Zr-DFO-trastuzumab and $^{89}$Zr-DFO-cetuximab without further manipulation. The results of radiochemistry studies are summarized in Tables 7-9. Using $^{89}$ZrCl$_4$ both radiopharmaceuticals were prepared in 15 minutes, with radiochemical purities and yields greater than 97%.

TABLE 7

Comparison of $^{89}$Zr(ox)$_2$ and $^{89}$ZrCl$_4$ used to prepare $^{89}$Zr-immuno-PET agents

| Parameter | $^{89}$Zr(ox)$_2$ | | | $^{89}$ZrCl$_4$ |
|---|---|---|---|---|
| | Perk et al.* | Knight et al.† | This work | This work |
| mAh (mg)‡ | 0.7-3.0 | 0.1 | 0.35 | 0.25 |
| $^{89}$Zr added (MBq) | 37-250 | 10 | 40-45 | 40-45 |
| Oxalic acid neutralization method | 2M Na$_2$CO$_3$ | 1M Na$_2$CO$_3$ | 2M Na$_2$CO$_3$ | None |
| Reaction buffer | 0.5M HEPES§ | PBS" | 0.5M HEPES§ | 0.5M HEPES§ |
| Final reaction pH | 6.8-7.2 | 7-8 | 6.8-7.2 | 6.8-7.2 |
| Reaction temperature (° C.) | 21-24 | 21-24 | 21-24 | 21-24 |
| Reaction time (h) | 1 | 1 | 1 | 0.25 |
| Radiolabeling yield (%) | >80 | 96.9 ± 3.3 | ≥95¶ | ≥97.5¶ |
| Radiochemical purity (%) | >95 | >95 | ≥96¶ | ≥97.5¶ |
| Specific activity (A$_s$; MBq µg$^{-1}$) | 0.067-0.086 | 0.1 ± 0.03 | 0.105 ± 0.003 (n = 10) # | 0.174 ± 0.003 (n = 10) # |

*Adapted from Perk, L. R. et al. *Eur. J. Nucl. Med. Mol. Imaging* 37, 250-259 (2010)

†Adapted from Knight, J. C. et al. Dalton Trans. 45, 6343-6347 (2016).

‡Mass mAb used in radiochemical synthesis.

§pH 7.1-7.3.

"pH 7.4.

¶Unchelated $^{89}$Zr was not present in the original reaction mixture as determined by Radio-ITLC. Final purity and yield reflect the presence of high and low molecular weight species, which were additionally determined by SEC.

$^{89}$Zr-DFO-trastuzumab (n = 5) and $^{89}$Zr-DFO-cetuximab (n = 5).

TABLE 8

Summary of optimized mAb mass and $^{89}$Zr(ox)$_2$ activity used to prepare
$^{89}$Zr-DFO-mAbs$^a$ (n = 3 for each radiopharmaceutical at each mAb mass)

| Conjugates (DFO-mAbs) | Mass of conjugate (µg) | $^{89}$Zr—Zr (ox)$_2$ added (MBq) | Radiochemical purity$^b$ by Radio-ITLC (%) | Radiochemical yield$^c$ (%) | Radiochemical purity$^c$ by SE-HPLC (%) | Specific activity (A$_s$; MBq µg$^{-1}$) |
|---|---|---|---|---|---|---|
| DFO-cetuximab | 500 | 43.2 | 99.8 ± 0.1 | 98.2 ± 0.3 | 98.3 ± 0.2 | 0.085 ± 0.003 |
| | 400 | 41.1 | 90.7 ± 0.2 | 95.6 ± 0.4 | 97.9 ± 0.1 | 0.098 ± 0.002 |
| | 350 | 40.5 | 99.6 ± 0.3 | 95.3 ± 0.1 | 96.5 ± 0.2 | 0.105 ± 0.003 |
| | 300 | 40.2 | 98.7 ± 0.3 | 88.3 ± 0.2 | 95.1 ± 0.3 | 0.118 ± 0.003 |
| | 250 | 39.5 | 97.9 ± 0.1 | 80.1 ± 0.4 | 91.5 ± 0.4 | 0.126 ± 0.002 |
| DFO-trastuzumab | 500 | 43.4 | 99.9 ± 0.1 | 98.1 ± 0.1 | 98.4 ± 0.3 | 0.085 ± 0.004 |
| | 400 | 41.3 | 99.8 ± 0.1 | 95.4 ± 0.3 | 97.9 ± 0.2 | 0.099 ± 0.003 |
| | 350 | 40.3 | 99.7 ± 0.2 | 95.2 ± 9.2 | 96.4 ± 0.3 | 0.105 ± 0.004 |
| | 300 | 40.1 | 98.5 ± 0.3 | 88.4 ± 0.4 | 94.7 ± 0.4 | 0.118 ± 0.002 |
| | 250 | 39.6 | 98.1 ± 0.2 | 79.9 ± 0.5 | 90.9 ± 0.6 | 0.125 ± 0.003 |

$^a$DFO-mAbs were labeled with $^{89}$Zr(ox)$_2$ using 2M Na$_2$CO$_3$ (20-25 µL), 0.5M HEPES buffer (500 µL, pH 7.2) and L-methionine (200 µL, 5 mg · mL$^{-1}$ in 0.25M sodium acetate, pH 6.8-7.0) at 21° C. for 1 h.
$^b$Unchelated $^{89}$Zr was not present in the original reaction mixture as determined by Radio-ITLC.
$^c$Final purity and yield reflect the presence of high and low molecular weight species, which were additionally determined by SEC.

The in vitro stability of [89]Zr-DFO-trastuzumab and [89]Zr-DFO-cetuximab was examined using centrifugal filtration analysis with gamma counting (Table 10-11), radio-ITLC (Tables 12 and 13) and radio-SEC (Tables 14 and 15) after being prepared with [89]ZrCl$_4$, and formulated in 20 mM histidine/240 mM sucrose buffer, 0.25 M sodium acetate (NaOAc) buffer containing 5 mg.·mL$^{-1}$ NAC or 0.25 M NaOAc containing 5 mg.·mL$^{-1}$ L-MET. When formulated in 20 mM histidine/240 mM sucrose buffer and stored at 21° C., both radiopharmaceuticals remained stable for 6 hours, with radiochemical impurities comprising less than 5% of the total reaction mixture. By 1 d however, purity decreased to 90%, and continued to decrease throughout the study. When both radiopharmaceuticals were formulated in 0.25 M NaOAc buffer containing 5 mg.·mL$^{-1}$ NAC and stored at 21° C., radiopharmaceutical purity remained above 95% for 24 h, but declined to 80% by the end of the study. When [89]Zr-DFO-trastuzumab was formulated in 0.25 M NaOAc containing 5 mg.·mL$^{-1}$ L-MET and stored at 21° C., radiopharmaceutical purity, as assessed by radio-SEC, remained above 95% for 3 days (average % intact at 3 d; 20 mM histidine/240 mM sucrose vs. 0.25 M NaOAc/5 mg.·mL$^{-1}$ NAC vs. 0.25 M NaOAc/5 mg.·mL$^{-1}$ L-MET; [one-way ANOVA]: 74.9±0.4 vs. 85.3±0.2 vs. 95.5±0.1; [F (3208, 0.99)=635.1, p<0.0001]). This result was recapitulated with [89]Zr-DFO-cetuximab (average % intact at 3 d; 20 mM histidine/240 mM sucrose vs. 0.25 M NaOAc/5 mg.·mL$^{-1}$ NAC vs. 0.25 M NaOAc/5 mg.·mL$^{-1}$ L-MET; [one-way ANOVA]: 64.1±0.5 vs. 88.7±0.1 vs. 95.1±0.1; [F (9914, 0.999)=1609, p<0.0001]). Finally, both radiopharmaceuticals, which were initially formulated in 0.25 M NaOAc containing 5 mg·mL$^{-1}$ L-MET, were stable in human serum over 7 days. Serum-associated radioactivity comprised less than 5% of the total reaction mixture at the end of the study (Table 16).

TABLE 10

Chronological stability study of [89]Zr-DFO-cetuximab formulated in different buffer-excipient combinations by centrifugal filter analysis (n = 3 for each buffer-excipient combination at each time point)

| Time point | Temp. (° C.) | Intact radiotracer % | | |
| --- | --- | --- | --- | --- |
| | | 20 mM Histidine/ 240 mM Sucrose | 0.25M NaOAc + 5 mg · mL$^{-1}$ NAC[a] | 0.25M NaOAc + 5 mg · mL$^{-1}$ L-MET[b] |
| 0 h | 21 | 99.6 ± 0.1 | 99.8 ± 0.1 | 99.8 ± 0.0 |
| 2 h | 4 | 99.7 ± 0.0 | 99.8 ± 0.0 | 99.7 ± 0.0 |
| | 21 | 99.5 ± 0.0 | 99.6 ± 0.0 | 99.5 ± 0.1 |
| 6 h | 4 | 99.5 ± 0.0 | 99.7 ± 0.0 | 99.7 ± 0.0 |
| | 21 | 98.3 ± 0.1 | 99.0 ± 0.0 | 99.4 ± 0.0 |
| 1 d | 4 | 98.2 ± 0.0 | 99.2 ± 0.1 | 99.5 ± 0.0 |
| | 21 | 90.9 ± 0.1 | 96.1 ± 0.0 | 99.4 ± 0.1 |
| 3 d | 4 | 92.7 ± 0.4 | 97.7 ± 0.3 | 98.8 ± 0.2 |
| | 21 | 74.3 ± 0.3 | 89.1 ± 0.9 | 98.4 ± 0.2 |
| 5 d | 4 | 88.5 ± 0.5 | 96.5 ± 0.2 | 98.0 ± 0.4 |
| | 21 | 65.4 ± 1.9 | 84.4 ± 1.1 | 96.7 ± 0.0 |
| 7 d | 4 | 84.4 ± 0.4 | 95.2 ± 0.1 | 97.7 ± 0.4 |
| | 21 | 60.4 ± 2.1 | 81.6 ± 1.9 | 96.3 ± 0.7 |

[a]N-acetyl-L-cysteine.

[b]L-Methionine.

TABLE 9

Summary of optimized mAb mass and [89]ZrCl$_4$ activity used to prepare [89]Zr-DFO-mAbs[a] (n = 3 for each radiopharmaceutical at each mAb mass)

| Conjugates (DFO-mAbs) | Mass of conjugate (μg) | [89]ZrCl$_4$ added (MBq) | Radiochemical purity[b] by Radio-ITLC (%) | Radiochemical yield[c] (%) | Radiochemical purity[c] by SE-HPLC (%) | Specific activity (A$_s$; MBq μg$^{-1}$) |
| --- | --- | --- | --- | --- | --- | --- |
| DFO-cetuximab | 500 | 43.8 | 99.9 ± 0.1 | 99.1 ± 0.3 | 98.6 ± 0.3 | 0.086 ± 0.005 |
| | 400 | 44.4 | 99.8 ± 0.3 | 98.5 ± 0.2 | 98.1 ± 0.4 | 0.109 ± 0.002 |
| | 300 | 42.8 | 99.9 ± 0.1 | 97.9 ± 0.1 | 97.8 ± 0.2 | 0.139 ± 0.004 |
| | 250 | 44.4 | 99.9 ± 0.2 | 97.7 ± 0.2 | 97.6 ± 0.1 | 0.174 ± 0.003 |
| | 200 | 41.6 | 99.7 ± 0.2 | 95.1 ± 0.4 | 95.5 ± 0.6 | 0.197 ± 0.001 |
| | 150 | 39.2 | 99.8 ± 0.1 | 93.9 ± 0.5 | 94.1 ± 0.7 | 0.245 ± 0.005 |
| DFO-trastuzumab | 500 | 43.5 | 99.9 ± 0.2 | 98.9 ± 0.1 | 98.7 ± 0.2 | 0.086 ± 0.004 |
| | 400 | 44.3 | 99.7 ± 0.2 | 98.4 ± 0.3 | 98.2 ± 0.5 | 0.108 ± 0.005 |
| | 350 | 42.7 | 99.8 ± 0.1 | 97.7 ± 0.2 | 97.1 ± 0.3 | 0.139 ± 0.002 |
| | 300 | 44.1 | 99.9 ± 0.1 | 97.5 ± 0.4 | 97.7 ± 0.1 | 0.172 ± 0.003 |
| | 250 | 41.8 | 99.9 ± 0.1 | 94.9 ± 0.5 | 94.9 ± 0.7 | 0.198 ± 0.005 |
| | 150 | 39.5 | 99.8 ± 0.1 | 93.4 ± 0.3 | 93.6 ± 0.5 | 0.246 ± 0.003 |

[a]DFO-mAbs were labeled with [89]ZrCl$_4$ using 0.5M HEPES buffer (500 μL, pH 7.2) and L-methionine (200 μL, 5 mg · mL$^{-1}$ in 0.25M sodium acetate, pH 6.8-7.0) at 21° C. for 15 min.

[b]Unchelated [89]Zr was not present in the original reaction mixture as determined by Radio-ITLC.

[c]Final purity and yield reflect the presence of high and low molecular weight species, which were additionally determined by SEC.

TABLE 11

Chronological stability study of $^{89}$Zr-DFO-trastuzumab formulated in different buffer-excipient combinations by centrifugal filtration analysis (n = 3 for each buffer-excipient combination at each time point)

| | | Intact radiotracer % | | |
|---|---|---|---|---|
| Time point | Temp. (° C.) | 20 mM Histidine/ 240 mM Sucrose | 0.25M NaOAc + 5 mg · mL$^{-1}$ NAC[a] | 0.25M NaOAc + 5 mg · mL$^{-1}$ L-MET |
| 0 h | 21 | 99.5 ± 0.1 | 99.8 ± 0.0 | 99.8 ± 0.0 |
| 2 h | 4 | 98.7 ± 0.0 | 99.7 ± 0.0 | 99.8 ± 0.0 |
| | 21 | 97.4 ± 0.3 | 99.6 ± 0.0 | 99.7 ± 0.0 |
| 6 h | 4 | 97.8 ± 0.1 | 99.7 ± 0.0 | 99.8 ± 0.0 |
| | 21 | 96.7 ± 0.4 | 98.9 ± 0.6 | 99.5 ± 0.1 |
| 1 d | 4 | 97.3 ± 0.0 | 99.2 ± 0.0 | 99.3 ± 0.0 |
| | 21 | 93.7 ± 0.3 | 95.8 ± 0.1 | 99.1 ± 0.2 |
| 3 d | 4 | 93.2 ± 0.4 | 98.2 ± 0.0 | 98.1 ± 0.0 |
| | 21 | 78.8 ± 0.7 | 87.8 ± 0.2 | 97.9 ± 0.3 |
| 5 d | 4 | 88.9 ± 0.8 | 96.9 ± 0.1 | 97.6 ± 0.2 |
| | 21 | 68.9 ± 2.0 | 83.4 ± 0.4 | 96.4 ± 1.8 |
| 7 d | 4 | 83.6 ± 1.6 | 95.5 ± 0.8 | 97.0 ± 0.2 |
| | 21 | 61.1 ± 3.5 | 80.1 ± 0.1 | 95.6 ± 0.5 |

[a]N-acetyl-L-cysteine.
[b]L-Methionine.

TABLE 12

Chronological stability study of $^{89}$ZrDFO-cetuximab formulated in different buffer-excipient combinations and analyzed by Radio-ITLC (n = 3 for each buffer-excipient combination at each time point)

| | | Intact radiotracer % | | |
|---|---|---|---|---|
| Time point | Temp. (° C.) | 20 mM Histidine/ 240 mM Sucrose | 0.25M NaOAc + 5 mg · mL$^{-1}$ NAC[a] | 0.25M NaOAc + 5 mg · mL$^{-1}$ L-MET[b] |
| 0 h | 21 | 99.9 ± 0.0 | 99.9 ± 0.1 | 99.9 ± 0.1 |
| 2 h | 4 | 99.7 ± 0.0 | 99.8 ± 0.1 | 99.9 ± 0.1 |
| | 21 | 99.2 ± 0.0 | 99.5 ± 0.1 | 99.8 ± 0.1 |
| 6 h | 4 | 98.7 ± 0.4 | 99.8 ± 0.0 | 99.8 ± 0.2 |
| | 21 | 98.2 ± 0.2 | 98.9 ± 0.3 | 99.5 ± 0.1 |
| 1 d | 4 | 97.5 ± 0.5 | 99.0 ± 0.2 | 99.4 ± 0.2 |
| | 21 | 90.8 ± 0.3 | 96.4 ± 0.6 | 99.2 ± 0.4 |

TABLE 12-continued

Chronological stability study of $^{89}$ZrDFO-cetuximab formulated in different buffer-excipient combinations and analyzed by Radio-ITLC (n = 3 for each buffer-excipient combination at each time point)

| | | Intact radiotracer % | | |
|---|---|---|---|---|
| Time point | Temp. (° C.) | 20 mM Histidine/ 240 mM Sucrose | 0.25M NaOAc + 5 mg · mL$^{-1}$ NAC[a] | 0.25M NaOAc + 5 mg · mL$^{-1}$ L-MET[b] |
| 3 d | 4 | 92.9 ± 1.2 | 97.9 ± 0.0 | 98.9 ± 0.0 |
| | 21 | 71.8 ± 2.9 | 92.1 ± 1.1 | 98.1 ± 0.5 |
| 5 d | 4 | 90.1 ± 0.4 | 96.7 ± 0.1 | 98.5 ± 0.0 |
| | 21 | 64.6 ± 0.6 | 86.1 ± 1.7 | 96.9 ± 0.1 |
| 7 d | 4 | 84.6 ± 2.8 | 95.8 ± 0.4 | 97.9 ± 0.3 |
| | 21 | 57.3 ± 2.5 | 81.1 ± 3.5 | 96.0 ± 0.1 |

[a]N-acetyl-L-cysteine.
[b]L-Methionine.

TABLE 13

Chronological stability study of $^{89}$Zr-DFO-trastuzumab formulated in different buffer-excipient combinations and analyzed by Radio-ITLC (n = 3 for each buffer-excipient combination at each time point)

| | | Intact radiotracer % | | |
|---|---|---|---|---|
| Time point | Temp. (° C.) | 20 mM Histidine/ 240 mM Sucrose | 0.25M NaOAc + 5 mg · mL$^{-1}$ NAC[a] | 0.25M NaOAc + 5 mg · mL$^{-1}$ L-MET |
| 0 h | 21 | 99.9 ± 0.1 | 99.9 ± 0.0 | 99.9 ± 0.1 |
| 2 h | 4 | 98.9 ± 0.2 | 99.4 ± 0.3 | 99.8 ± 0.1 |
| | 21 | 97.7 ± 0.3 | 99.1 ± 0.1 | 99.8 ± 0.2 |
| 6 h | 4 | 97.8 ± 0.0 | 98.9 ± 0.3 | 99.9 ± 0.0 |
| | 21 | 97.0 ± 0.1 | 98.0 ± 0.4 | 99.7 ± 0.1 |
| 1 d | 4 | 96.5 ± 0.4 | 98.2 ± 0.0 | 99.7 ± 0.0 |
| | 21 | 93.3 ± 1.4 | 96.8 ± 0.4 | 99.6 ± 0.0 |
| 3 d | 4 | 90.2 ± 1.1 | 97.6 ± 0.2 | 99.0 ± 0.2 |
| | 21 | 81.0 ± 1.3 | 87.7 ± 0.5 | 98.6 ± 0.3 |
| 5 d | 4 | 88.3 ± 1.7 | 96.5 ± 0.3 | 98.4 ± 0.2 |
| | 21 | 74.3 ± 2.3 | 84.0 ± 0.1 | 97.9 ± 0.1 |
| 7 d | 4 | 83.3 ± 1.2 | 95.1 ± 0.2 | 97.8 ± 0.0 |
| | 21 | 69.4 ± 3.9 | 79.9 ± 1.0 | 97.5 ± 0.2 |

[a]N-acetyl-L-cysteine.
[b]L-Methionine.

TABLE 14

Chronological stability analysis of $^{89}$Zr-DFO-cetuximab formulated in different buffer-excipient combinations as determined by size exclusion chromatography (n = 3 for each buffer-excipient combination at each time point)

| | | Species % | | | | | | | | |
|---|---|---|---|---|---|---|---|---|---|---|
| | | 20 mM Histidine/ 240 mM Sucrose | | | 0.25M NaOAc + 5 mg · mL$^{-1}$ NAC[a] | | | 0.25M NaOAc + 5 mg · mL$^{-1}$ L-MET[b] | | |
| Time point | Temp. (° C.) | HMW[c] | Intact radiotracer | LMW[d] | HMW[c] | Intact radiotracer | LMW[d] | HMW[c] | Intact radiotracer | LMW[d] |
| 0 h | 21 | 4.4 ± 0.6 | 95.4 ± 0.1 | 0.0 | 2.5 ± 0.2 | 97.8 ± 0.3 | 0.0 | 2.1 ± 0.2 | 97.6 ± 0.1 | 0.0 |
| 1 d | 4 | 6.2 ± 2.0 | 88.8 ± 0.3 | 5.0 ± 1.5 | 3.3 ± 0.2 | 95.7 ± 0.3 | 1.1 ± 0.1 | 3.7 ± 0.1 | 96.2 ± 0.1 | 0.1 ± 0.0 |
| | 21 | 5.6 ± 0.5 | 82.1 ± 0.6 | 12.2 ± 0.1 | 1.7 ± 0.2 | 94.5 ± 0.1 | 3.8 ± 0.1 | 3.8 ± 0.1 | 95.9 ± 0.1 | 0.3 ± 0.0 |
| 3 d | 4 | 8.8 ± 1.3 | 81.3 ± 0.1 | 9.9 ± 1.1 | 3.4 ± 0.1 | 93.6 ± 0.4 | 3.0 ± 0.3 | 4.2 ± 0.1 | 95.5 ± 0.1 | 0.5 ± 0.1 |
| | 21 | 3.3 ± 0.1 | 64.1 ± 0.5 | 32.7 ± 0.7 | 1.8 ± 0.2 | 88.7 ± 0.1 | 9.4 ± 0.1 | 3.8 ± 0.1 | 95.1 ± 0.1 | 1.2 ± 0.1 |
| 5 d | 4 | 7.0 ± 0.5 | 76.9 ± 0.3 | 16.1 ± 0.7 | 3.8 ± 0.4 | 91.3 ± 0.4 | 4.9 ± 0.1 | 3.8 ± 0.1 | 92.5 ± 0.2 | 1.7 ± 0.1 |
| | 21 | 2.8 ± 0.2 | 53.8 ± 0.2 | 43.4 ± 0.2 | 1.3 ± 0.1 | 84.4 ± 0.1 | 14.2 ± 0.2 | 3.9 ± 0.2 | 92.9 ± 0.1 | 3.2 ± 0.2 |
| 7 d | 4 | 6.9 ± 0.3 | 73.6 ± 0.6 | 19.5 ± 0.8 | 3.6 ± 0.1 | 89.9 ± 0.3 | 6.5 ± 0.1 | 6.8 ± 0.1 | 91.3 ± 0.1 | 1.9 ± 0.1 |
| | 21 | 2.5 ± 0.1 | 49.7 ± 1.1 | 47.8 ± 1.1 | 1.3 ± 0.2 | 74.1 ± 0.3 | 24.6 ± 0.3 | 3.9 ± 0.1 | 91.8 ± 0.3 | 4.3 ± 0.0 |

[a]N-acetyl-L-cysteine.
[b]L-Methionine.
[c]High-molecular weight, radioactive protein species.
[d]Low-molecular weight, radioactive protein species, or unchelated $^{89}$Zr.

TABLE 15

Chronological stability analysis of $^{89}$Zr-DFO-trastuzumab formulated in different buffer-excipient combinations as determined by size exclusion chromatography (n = 3 for each buffer-excipient combination as each time point)

| | | Species % | | | | | | | | |
|---|---|---|---|---|---|---|---|---|---|---|
| | | 20 mM Histidine/ 240 mM Sucrose | | | 0.25M NaOAc + 5 mg · mL$^{-1}$ NAC$^a$ | | | 0.25M NaOAc + 5 mg · mL$^{-1}$ L-MET$^b$ | | |
| Time point | Temp. (° C.) | HMW$^c$ | Intact radiotracer | LMW$^d$ | HMW$^c$ | Intact radiotracer | LMW$^d$ | HMW$^c$ | Intact radiotracer | LMW$^d$ |
| 0 h | 21 | 3.9 ± 0.3 | 96.1 ± 0.2 | 0.0 | 2.3 ± 0.1 | 97.7 ± 0.1 | 0.0 | 2.4 ± 0.1 | 97.7 ± 0.1 | 0.0 |
| 1 d | 4 | 3.7 ± 0.1 | 90.6 ± 0.6 | 5.7 ± 0.6 | 2.8 ± 0.3 | 96.2 ± 0.3 | 1.1 ± 0.1 | 2.7 ± 0.0 | 97.0 ± 0.0 | 0.3 ± 0.0 |
| | 21 | 2.7 ± 0.2 | 88.0 ± 0.2 | 9.3 ± 0.5 | 1.6 ± 0.1 | 92.6 ± 0.2 | 5.8 ± 0.1 | 2.9 ± 0.1 | 96.8 ± 0.1 | 0.3 ± 0.0 |
| 3 d | 4 | 3.6 ± 0.4 | 84.5 ± 0.2 | 11.9 ± 0.2 | 3.5 ± 0.1 | 93.5 ± 0.1 | 2.9 ± 0.1 | 3.9 ± 0.2 | 95.3 ± 0.2 | 0.8 ± 0.0 |
| | 21 | 2.1 ± 0.2 | 74.9 ± 0.4 | 23.0 ± 0.7 | 1.4 ± 0.2 | 85.3 ± 0.2 | 13.3 ± 0.1 | 3.3 ± 0.0 | 95.5 ± 0.1 | 1.5 ± 0.1 |
| 5 d | 4 | 3.7 ± 0.1 | 81.6 ± 0.5 | 14.6 ± 0.6 | 3.8 ± 0.1 | 91.8 ± 0.3 | 4.4 ± 0.4 | 5.2 ± 0.3 | 92.4 ± 0.5 | 2.4 ± 0.3 |
| | 21 | 2.0 ± 0.1 | 60.5 ± 0.7 | 37.5 ± 0.8 | 1.3 ± 0.2 | 80.4 ± 0.3 | 18.3 ± 0.5 | 4.0 ± 0.1 | 92.6 ± 0.2 | 3.4 ± 0.1 |
| 7 h | 4 | 3.7 ± 0.3 | 77.2 ± 0.7 | 19.2 ± 1.0 | 4.2 ± 0.1 | 90.4 ± 0.4 | 5.8 ± 0.4 | 4.9 ± 0.2 | 91.9 ± 0.0 | 3.2 ± 0.1 |
| | 21 | 1.8 ± 0.1 | 56.5 ± 0.1 | 41.7 ± 0.2 | 1.3 ± 0.3 | 73.6 ± 0.3 | 25.1 ± 0.0 | 3.9 ± 0.4 | 91.1 ± 0.1 | 5.0 ± 0.3 |

$^a$N-acetyl-L-cysteine.
$^b$L-Methionine.
$^c$High-molecular weight, radioactive protein species.
$^d$Low-molecular weight, radioactive protein species, or unchelated $^{89}$Zr.

TABLE 16

Chronological in vitro serum stability study data of $^{89}$Zr-DFO-mAbs maintained at 37° C. (n = 3 for each radiopharmaceutical at each time point)

| | $^{89}$Zr—Zr-DFO-cetuximab | | $^{89}$Zr—Zr-DFO-trastuzumab | |
|---|---|---|---|---|
| Time point | % Intact | % Unchelated $^{89}$Zr | % Intact | % Unchelated $^{89}$Zr |
| 0 h | 99.8 ± 0.1 | 0.2 ± 0.0 | 99.8 ± 0.1 | 0.2 ± 0.0 |
| 1 d | 99.2 ± 0.2 | 0.7 ± 0.1 | 98.9 ± 0.3 | 1.0 ± 0.1 |
| 3 d | 98.3 ± 0.3 | 1.6 ± 0.4 | 98.1 ± 0.2 | 1.9 ± 0.3 |
| 5 d | 97.4 ± 0.5 | 2.6 ± 0.3 | 97.2 ± 0.4 | 2.7 ± 0.2 |
| 7 d | 96.7 ± 0.4 | 3.4 ± 0.5 | 96.4 ± 0.5 | 3.5 ± 0.3 |

$^{89}$Zr-DFO-trastuzumab, prepared with $^{89}$ZrCl$_4$ or $^{89}$Zr(ox)$_2$, was evaluated using the Lindmo method. $^{89}$Zr-DFO-trastuzumab prepared with $^{89}$Zr(ox)$_2$ demonstrated $K_a$, $B_{max}$ and IR values of 2.2 × 10$^8$ M$^{-1}$, 1.3 × 10$^8$ binding sites per cell and 1.0, respectively. $^{89}$Zr-DFO-trastuzumab prepared with $^{89}$ZrCl$_4$ demonstrated $K_a$, $B_{max}$ and IR values of 2.4 × 10$^8$ M$^{-1}$, 1.3 × 10$^8$ sites per cell and 0.91, respectively (Table 17). No binding was observed in the HER2$^-$ 827 cell line.

Small animal PET/CT imaging was performed; HER2$^+$ tumors retained more radioactivity than HER2$^-$ tumors at 144 h p.i. (HER2$^+$ tumor vs. HER2$^-$ tumor; % ID/g ± SD, p value: tumor, 29.5 ± 4.9 vs. 16.7 ± 6.1, 0.0011) but differences in tumor-associated radioactivity among mice receiving $^{89}$Zr-DFO-trastuzumab prepared with either $^{89}$ZrCl$_4$ or $^{89}$Zr(ox)$_2$ were not significantly different (p = 0.30). Additionally, the biodistribution of radioactivity in non-target tissues between both cohorts was similar. For example, the amount of radioactivity in the bones of mice injected with $^{89}$Zr-DFO-trastuzumab prepared with $^{89}$ZrCl$_4$ was 8.3 ± 0.5%, while it was 7.8 ± 0.9% for mice receiving $^{89}$Zr-DFO-trastuzumab prepared with $^{89}$Zr(ox)$_2$ (Table 18).

TABLE 17

In vitro binding data for $^{89}$Zr-DFO-trastuzumab prepared with either $^{89}$Zr(ox)$_2$ or $^{89}$ZrCl$_4$ (n = 5 for each radiopharmaceutical)

| Binding characteristics in HER2$^+$ 2170 lung cancer cells | $^{89}$Zr(ox)$_2$ | $^{89}$ZrCl$_4$ |
|---|---|---|
| Affinity constant (K$_a$) | 2.15 × 10$^8$ M$^{-1}$ | 2.43 × 10$^8$ M$^{-1}$ |
| Binding sites per cell (B$_{max}$) | 1.29 × 10$^8$ | 1.34 × 10$^8$ |
| Immunoreactivity (IR) | 1.02 | 0.91 |

TABLE 18

Post-PET biodistribution (% ID/g) of $^{89}$Zr-DFO-trastuzumab prepared with $^{89}$Zr(ox)$_2$ or $^{89}$ZrCl$_4$ in selected organs at 144 p.i. (n = 5/group)

| Tissue/Organ | $^{89}$Zr—Zr-DFO-trastuzumab prepared with $^{89}$Zr—Zr(ox)$_2$ | $^{89}$Zr—Zr-DFO-trastuzumab prepared with $^{89}$Zr—ZrCl$_4$ |
|---|---|---|
| Blood | 6.8 ± 1.3 | 6.5 ± 1.3 |
| Heart | 1.9 ± 0.4 | 1.5 ± 0.2 |
| Lung | 5.2 ± 0.7 | 4.3 ± 0.5 |
| Liver | 4.9 ± 0.7 | 4.2 ± 0.3 |
| Small intestine | 1.1 ± 0.2 | 0.8 ± 0.1 |
| Large intestine | 1.3 ± 0.2 | 1.1 ± 0.1 |
| Kidney | 5.1 ± 0.5 | 4.6 ± 0.3 |
| Spleen | 11.2 ± 1.3 | 8.3 ± 0.8 |
| Pancreas | 0.8 ± 0.1 | 0.8 ± 0.1 |
| Stomach | 0.8 ± 0.3 | 0.6 ± 0.3 |
| Muscle | 0.5 ± 0.1 | 0.5 ± 0.1 |
| Fat | 0.6 ± 0.1 | 0.7 ± 0.2 |
| Bone | 7.8 ± 0.9 | 8.3 ± 0.5 |
| Tumor (+) | 32.8 ± 4.4 | 29.5 ± 4.9 |
| Tumor (−) | 17.0 ± 3.0 | 16.7 ± 6.1 |

It will be appreciated by persons skilled in the art that the invention described herein is not limited to what has been particularly shown and described. Rather, the scope of the fiber is defined by the claims which follow. It should further be understood that the above description is only representative of illustrative examples of embodiments. The description has not attempted to exhaustively enumerate all possible variations. The alternate embodiments may not have been presented for a specific portion of the fiber and may result from a different combination of described portions, or that other un-described alternate embodiments may be available for a portion, is not to be considered a disclaimer of those alternate embodiments. It will be appreciated that many of those un-described embodiments are within the literal scope of the following claims, and others are equivalent.

The invention claimed is:

1. A radiopharmaceutical system comprising a complex and an effective amount of a radioprotectant for stabilizing the complex, wherein
   (a) the complex comprises a $^{89}$Zr-labeled conjugate comprising $^{89}$Zr coordinated to a chelator, and wherein the chelator is conjugated to an antibody selected from cetuximab or trastuzumab, wherein the chelator is selected from the group consisting of desferrioxamine B (DFO) and derivatives thereof; and (b) the radioprotectant comprises an effective amount of N-acetyl-L-cysteine.

2. The system of claim 1, wherein the chelator is conjugated to a monoclonal antibody, wherein the ratio between the chelator and the monoclonal antibody ranges from about 4:1 to about 2:1.

3. The system of claim 1, wherein the complex has a specific activity of at least about 0.14 MBq/μg.

4. The system of claim 1, wherein the complex has a purity of at least about 97% for 7 days in the presence of the radioprotectant.

5. A method of preparing a complex of claim 1, wherein the complex comprises $_{89}Zr$ coordinated to a chelator, wherein the chelator is desferrioxamine B (DFO) or a derivative thereof, and the chelator is conjugated to an antibody selected from cetuximab or trastuzumab, comprising the steps of a) reacting the chelator with cetuximab or trastuzumab to form a conjugate;

b) mixing the $^{89}Zr$ with the conjugate to form a reaction mixture, wherein the reaction mixture is free from treatment of a base;

c) incubating the reaction mixture to form a crude $^{89}Zr$-labeled conjugate; and d) purifying the crude $^{89}Zr$-labeled conjugate.

6. The method of claim 5, wherein prior to forming the conjugate, the chelator and the antibody are in a ratio of about 5:1.

7. The method of claim 5, wherein the conjugate comprises the chelator and the antibody in a ratio ranging from about 4:1 to about 2:1.

8. The method of claim 5, wherein prior to forming the complex, the conjugate and the $^{89}Zr$ is in a ratio of about 2.5:1.

9. The method of claim 5, wherein the $^{89}Zr$ of step b) is in the form of an independent salt having a counter ion selected from the group consisting of chloride, oxalate, bromide, fluoride and acetyl acetonate (AcAc).

10. The method of claim 5, wherein the reaction mixture of step b) comprises N-acetyl-L-cysteine.

11. The method of claim 5, wherein step d) comprises passing the crude $^{89}Zr$-labeled conjugate through a column, wherein the crude $^{89}Zr$-labeled conjugate is eluted down the column with an eluting solution containing N-acetyl-L-cysteine.

12. The method of claim 5, further comprising adding N-acetyl-L-cysteine to the purified complex or a solution thereof.

13. A method of treating or diagnosing a disease comprising administering to a subject in need the radiopharmaceutical system of claim 1, wherein the disease is selected from the group consisting of cancer, cardiovascular, neurological, infectious, metabolic and autoimmune diseases.

14. The system of claim 1, wherein the complex has a % intact of at least about 97% for 7 days in the presence of the radioprotectant.

*   *   *   *   *